(12) United States Patent
Lopes

(10) Patent No.: US 6,559,110 B1
(45) Date of Patent: May 6, 2003

(54) SYNDET BAR SOAP HAVING AN ACIDIFYING AGENT

(76) Inventor: John A. Lopes, 2209 Niagara Dr., Troy, MI (US) 48083

( * ) Notice: Subject to any disclaimer, the term of this patent is extended or adjusted under 35 U.S.C. 154(b) by 0 days.

(21) Appl. No.: 09/935,930

(22) Filed: Aug. 23, 2001

Related U.S. Application Data

(60) Provisional application No. 60/227,358, filed on Aug. 24, 2000.

(51) Int. Cl.[7] .................................................. A61K 7/50
(52) U.S. Cl. ........................ 510/141; 510/152; 510/153; 510/155; 424/44; 424/49; 424/55; 424/70.1
(58) Field of Search .................................. 510/141, 152, 510/153, 155; 424/44, 49, 70.1, 55

(56) References Cited

U.S. PATENT DOCUMENTS 4,673,525 A * 6/1987 Small et al. ................. 252/132
5,691,287 A * 11/1997 Villars et al. ................ 510/151

* cited by examiner

*Primary Examiner*—Necholus Ogden

(57) ABSTRACT

A bar soap preparation having enhanced antibacterial and microbial properties which contains between 0.1 weight % and 95 weight % of at least one anionic surfactant; and at least one acidifying agent present in an amount sufficient to impart a pH of below 5.0. The bar soap provides microbial protection resulting from its rapid microbicidal action.

6 Claims, No Drawings

SYNDET BAR SOAP HAVING AN ACIDIFYING AGENT

CROSS REFERENCE TO CO-PENDING APPLICATION

This application claims the benefit of the priority date of co-pending Provisional Application Serial No. 60/227,358, filed Aug. 24, 2000, in the name of John A. Lopes, Ph.D., the entire contents of which are incorporated hereby by reference.

BACKGROUND OF THE INVENTION

1. Field of the Invention

The present intention relates to the preparation of synthetic detergent (syndet) bar soap composition useful for washing and cleaning hands and other body parts for preventing the risk of infections caused by microorganisms which can also be efficaciously employed on other sanitizable animate and inanimate surfaces. More particularly, this invention pertains to the preparation of acidic syndet bar soap compositions and the material which results therefrom.

2. Description of Related Art

Typically soaps are prepared under conditions at above neutral pH. Thus the pH may be neutral or alkaline during preparation. At such pH levels, microorganisms can remain viable on the contaminated soaps. These can be transferred to the surface being treated by the soap. Additionally, spoilage microorganisms can multiply on the soap. Antimicrobial agents are often incorporated into such soaps to prevent microbial growth. However, such antimicrobial agents do not exhibit full antimicrobial potential due to the neutral or alkaline pH of the surrounding environment.

Synthetic detergent (syndet) bar soaps, are based on detergency of surface-active agents (synthetic detergents) instead of alkali salt or fatty acids used in conventional soaps. Because syndet soaps clean and lather like conventional soaps, general public often refers to syndet type compositions simply as soaps. Surface active agents incorporated in hand and toilet soaps remove soil and dirt from the surface of the skin or hair along with some microorganisms. However, these soaps may not kill microorganisms. Bar soaps may be contaminated with bacteria and even transmit these microorganisms during their use. Thus the use of soaps without antibacterial properties may even add microorganisms to the skin surfaces and be a vector for transmission of infections. Thus, these soaps cannot be relied upon to prevent spread of infective germs.

Antibacterial and bactericidal soaps used for personal and health care applications typically are soaps which incorporate various antimicrobial agents in addition to the surface-active agents at pH greater than 7.0 (neutrality). Antibacterial agents are often incorporated in soaps to prevent growth of microorganisms in the soap rather than as effective agents for reducing or eliminating germs on the surfaces being cleaned.

Thus, soaps labeled as "antibacterial" may prevent or inhibit the growth of microorganisms on the soap surface or in the soap matrix but not offer protection by killing germs on the contact surfaces, such as skin, hair or the like. Such antibacterial soaps cannot be routinely classified as "sanitizing" soaps. Only a few types of antibacterial soaps can reduce microbial populations on the skin, hair or other body parts. These contain antibacterial agents specifically selected for such activity. These commonly used antibacterial ingredients include esters of para-hydroxybenzoic acid "parabens" (such as methyl parabens, propyl parabens, butyl parabens, and ethyl parabens), ethyl alcohol, imidazolidinyl urea, isothiazolin compounds, triclosan, dehydroacetate, o-phenyl phenol, quaternium compounds, boric acid, formaldehyde solutions, butylated hydroxyanisole (BHA), and butylated hydroxytoluene (BHT).

These materials typically are prepared and employed in compositions at neutral to alkaline pH. Fatty acid soaps must be prepared at neutral or alkaline conditions in order preserve the cleaning properties of the given soap. Synthetic detergent soaps are prepared in a similar manner as it has been held that neutral or alkaline pH levels are required to achieve proper cleaning characteristics of the soap material.

Conventional soap compositions for skin care which achieve suitable levels of sanitization are high in cost or are toxic. Chlorine based products are harmful to the environment; also certain chlorine based products are not available to the public except in health-care institutions. Thus, a sanitizing soap which would be environmentally friendly and less toxic would be highly desirable. It would also be desirable to provide a sanitizing soap which is economical and microbicidal for preventing surface or topical infection without the drawbacks of available sanitizing soap products.

Anionic surfactants have been proposed for use in cleaning compositions as well as in sanitizers or disinfecting solutions. However, for use as soap, the anionic surfactant must be present in sufficient amount to generate foam for cleaning purposes, such as washing hands and for general personal hygiene, facial conditioning, and the like. The use of high concentration anionic surfactants and other surfactant containing compositions at low pH has been held to result in damage to the skin, dryness, cracking, chapping, and irritation of the skin. Thus, anionic surfactants at low pH have not been used as microbicidal and sanitizing soaps on skin and body surfaces.

Additionally, some of the antimicrobial agents used in bar soaps, such as triclosan, have been reported to enhance antibiotic resistance in certain strains of bacteria. It is feared that their use could create the risk of propagating drug resistant bacteria and transmitting such bacteria to multiple users of the bar soap. Preparation of bar soap which would have antimicrobial properties but permit elimination or reduction in the use of such antimicrobial agents would be highly desirable.

The need to provide good lathering cleaning and sanitizing soaps is still largely unfilled. Thus, it would be desirable to provide a method for preparing a syndet soap having good cleaning characteristics which also has enhanced effective sanitizing attributes. It would also be desirable to provide syndet soaps which are acidic in nature and can exhibit antimicrobial properties. It would also be beneficial to provide a syndet bar soap which would permit the incorporation of materials, such as alpha-hydroxy acids, to facilitate and promote beneficial healing and rejuvenating of the skin.

SUMMARY OF INVENTION

The present invention is a synthetic detergent bar soap and method for making the same which is prepared under acidic conditions to enhance or provide antimicrobial properties to the material thus prepared. The material thus prepared exhibits at least one of the following advantages: a) under acidic conditions, the soap composition exhibits antimicrobial properties inhibiting survival and growth of microorganisms on the soap surface and on contact surfaces; b) the activity of antibacterial agents used in the soap can also be enhanced under acidic conditions; c) addition of alpha hydroxy-acids can also have beneficial effect in rejuvenating skin.

Thus the preparation of syndet soaps under acidic conditions can have cost savings or economic advantage in eliminating or reducing the amount or concentration of antimicrobial agents employed in the composition. Antimicrobial agents that are normally incorporated in antimicrobial soaps exhibit enhanced antimicrobial action under acidic conditions. Thus, the antimicrobial properties of materials already incorporated in the syndet bar soap can be further enhanced by addition of antimicrobial agents. Because of the enhanced antimicrobial activity under acidic conditions, the amount or concentration of antimicrobial agents can be reduced. This will provide an additional cost savings.

The soap composition consists essentially of:
a) an anionic surfactant present in an amount in the range from about 0.10 weight % to about 95.0 weight % based on the total weight of the concentrate composition; and
b) an acidifying agent present in an amount sufficient to provide a pH below 5.0.

DETAILED DESCRIPTION OF THE PREFERRED EMBODIMENT

The present invention is predicated on the unexpected discovery that an effective synthetic detergent bar soap can be prepared under acidic conditions which will exhibit antimicrobial characteristics. The syndet bar soap composition is based on (a) cleaning, surface active and sudsing properties of anionic surface active agent or agents, (b) enhancement of antimicrobial properties under acidic conditions, and (c) ready and effective incorporation of miscellaneous ingredients used to impart certain antibacterial, physical properties such as emollient, lubricating, foam boosting, binding, coloring, anti-cracking, perfuming, brightening, transparency, whitening, thixotropic, solubilizing, cleaning, antioxidant, skin nutritive as well as other organoleptic properties.

The soap composition of the present invention consists essentially of:
(a) at least one anionic surfactant present in an amount in the range from about 0.10 weight % to about 95 weight % based on the total weight of the concentrate composition; and
(b) at least one acidifying agent selected from acids of the group which includes acetic acid, adipic acid, ascorbic acid, benzoic acid, citric acid, dehydroacetic acid, erythorbic acid, fumaric acid, glutaric acid, gluconic acid, hyaluronic acid, hydroxyacetic acid, glycolic acid, lactic acid, malic acid, salicylic acid, sorbic acid, succinic acid, tannic acid, tartaric acid, sulfuric acid, phosphoric acid, nitric acid, hydrochloric acid, sulfamic acid, carboxylic acid polymers, homo- or heteropolymerized alpha-hydroxy carboxylic acids including poly lactic acid and poly lactic-glycolic acid and mixtures of two or more said acids, said acidifying agent being present in the concentrate composition in an amount sufficient to provide a pH below 5.0 in aqueous solution.

The bar soap composition of the present invention provides microbicidal protection resulting from its rapid microbicidal action. Typically, rapid microbicidal protection results from significant microbial reduction in an interval of 30 to 60 seconds. In certain instances, it is believed that reductions in an amount up to five logarithmic units may be possible depending upon the type of contact surface and target microorganism.

The composition may also include various other components to impart antibacterial, and other desirable physical and organoleptic properties to the syndet bar soap. These can include antibacterial agents, skin conditioning agents, lubricating agents, coloring agents, moisturizing agents, binding and anti-cracking agents, perfuming agents, brightening agents, UV absorbing agents, whitening agents, transparency imparting agents, thixotropic agents, solubilizing agents, abrasive agents, antioxidants, and skin healing agents. In the preferred embodiment, the syndet soap may contain one or more of these optional agents, with two or more being most preferred. The optional agents can be present in any amount up to 5.0% by weight by category; with an amount between 0.001 and 5.0% by weight being preferred.

The anionic surfactant may be present as a free acid, ester or salt form (e.g., the ammonium, sodium, potassium, calcium and magnesium salts) of a suitable anionic surfactant. Suitable anionic surfactants include at least one of the following:

(a) $C_6$–$C_{18}$ alkyl- and alkenyl-sulfates;
(b) $C_6$–$C_{18}$ alkyl- and alkenyl-ether sulfates;
(c) $C_6$–$C_{16}$ alkyl diphenyl ether disufonates;
(d) $C_4$–$C_{18}$ fatty acid isethionates;
(e) $C_6$–$C_{18}$ alkyl- and alkenyl sulfonates;
(f) dialkyl- and dialkenyl sulfosuccinates in which the alkyl or alkenyl groups independently contain from six to eighteen carbon atoms;
(g) alkyl benzene sulfonates in which alkyl group contains from $C_4$–$C_{18}$ carbon atoms;
(h) alkyl naphthalene sulfonates in which alkyl group contains from one to six carbon atoms;
(i) the mono-n-alkyl and mono-n-alkenyl acyl esters of $C_2$–$C_4$ hydroxylated monocarboxylic acids in which the alkyl or alkenyl group contains from six to eighteen carbon atoms;
(j) the mono-n-alkyl and mono-n-alkenyl alkyl esters of $C_2$–$C_4$ dicarboxylic acids in which the alkyl or alkenyl group contains six to eighteen carbon atoms; and
(k) $C_4$–$C_{16}$ fatty alcohol sulfoacetates.

By the term "alkyl" as used throughout this specification and the appended claims is meant a monovalent straight or branched chain hydrocarbon radical which can be thought of as derived from a saturated acyclic hydrocarbon by the removal of one hydrogen atom. By the term "alkenyl" is meant a monovalent hydrocarbon radical containing one or more carbon-carbon double bonds, which radical can be thought of as being derived from an unsaturated acyclic hydrocarbon by the removal of one hydrogen atom.

The term, "salt of a mono-(n-alkyl) or mono-(n-alkenyl) acyl ester of $C_2$–$C_4$ hydroxylated monocarboxylic acids" means an ester-salt of a hydroxylated monocarboxylic acid, such as lactic acid, which has been formed by esterification of its hydroxyl function by another acid, and in which its carboxyl function has been converted to a carboxylate salt. An example of such a compound is so-called "decyl lactylate" which is the ester formed by esterifying the hydroxyl group of lactic acid with decanoic acid, and converting the carboxyl function of the lactic acid portion of the resulting ester to the carboxylate salt form.

Similarly, the term, "salt of a mono-(n-alkyl) or mono(n-alkenyl)acyl ester of $C_2$–$C_4$ hydroxylated dicarboxylic acids" means an ester-salt or a hydroxylated dicarboxylic acid, such as hydroxymalonic acid, which has been formed by esterification of its hydroxyl function by another acid, and in which its two carboxyl functions have been converted to carboxylate salts.

By the term "salt of a mono-(n-alkyl) or mono(n-alkenyl) alkyl ester of $C_2$–$C_4$ dicarboxylic acids" is meant an ester-salt of dicarboxylic acid, such as succinic acid, which has been formed by esterification by an alcohol at one carboxyl group.

Preferred anionic surfactants for the compositions include free acids or the ammonium, sodium, potassium, calcium or magnesium salts of 1) alpha olefin ($C_{14}$–$C_{16}$) sulfonic acid; 2) $C_4$–$C_{18}$ fatty acid isethionic acid; 3) $C_4$–$C_{18}$ fatty alcohol sulfoacetic acid; 4) decyl lactylic acid; 5) lauryl sulfuric acid, and 6) 1,4-dihexyl sulfosuccinic acid.

The anionic surfactant may be present in any amount between about 0.10 weight % to 95.0 weight %. The specific amount employed would be determined by the specific use to which the soap is put and desirable characteristics such as lather formation, cleansing power, etc. to be achieved.

The acidifying agent is present in an amount sufficient to impart a pH at or below 5.0 and may be either organic or inorganic. The acidifying agent may be used individually or in any suitable combination of acids. The acidifying acid may be at least one of the following: includes one or more than one of the following: acetic acid, adipic acid, ascorbic acid, benzoic acid, citric acid, dehydroacetic acid, erythorbic acid, fumaric acid, glutaric acid, gluconic acid, hyaluronic acid, hydroxyacetic acid, lactic acid, malic acid, salicylic acid, sorbic acid, succinic acid, tannic acid, tartaric acid, sulfuric acid, phosphoric acid, nitric acid, hydrochloric acid, sulfamic acid, carboxylic acid polymers, homo- or hetero-polymerized alpha-hydroxy carboxylic acids including poly lactic acid and poly lactic-glycolic acid.

Preferably, the acidifying agent is at least one of acetic acid, adipic acid, ascorbic acid, benzoic acid, citric acid, dehydroacetic acid, erythorbic acid, fumaric acid, glutaric acid, gluconic acid, hyaluronic acid, hydroxyacetic acid, lactic acid, malic acid, salicylic acid, sorbic acid, succinic acid, tannic acid, or tartaric acid. Even more preferably, the acid is selected from the group which includes lactic acid, citric acid, ascorbic acid, erythorbic acid, malic acid and adipic acid.

As indicated above, the composition of the present invention may include other optional components added to impart additional antibacterial activity as well as other desirable characteristics including but not limited to biological, physical, organoleptic and other functional properties in the finished syndet bar composition. Each of the optional component classes are typically present in an amount between 0.001% and 5.0% w/w.

Examples of such component classes include antibacterial agents. Compounds suitable for use as antibacterial agents include at least one of benzoic acid, benzoic acid salts, esters of benzoic acid, sorbic acid, sorbic acid salts, esters of sorbic acid, esters of para hydroxy benzoic acid "parabens" (methyl, propyl, butyl and ethyl), chlorohexidine, ethyl alcohol, imidazolidinyl urea, isothiazolin compounds, triclosan, 3,4,4-trichlorocarbanilide, dehydroacetate, o-phenyl phenol, quaternium compounds, boric acid, formaldehyde solution, butylated hydroxyanisole (BHA) and butylated hydroxytoluene (BHT), fatty acids, fatty acid salts and esters of fatty acids, and antibacterial peptides including nisin and magnanin.

Examples of suitable optional components also include skin conditioning compounds. Suitable skin conditioning compounds include natural products such as plant oils, aloe vera, sea weed extracts, hydrolyzed protein products, lanolin and lanolin esters, vitamins, including vitamin A, C, D and E and their derivatives, fatty acid esters of carboxylic acids, alcohols and carbohydrates.

Lubricating agents which can be employed in the syndet soap of the present invention include natural polymers such as polysaccharide-based compounds, xanthan, arabic, ghatti, carrageenan gums; or other polymers such as starch, cellulose, fatty acid, fatty alcohols, alginic acid, dextrans, modified starch and cellulose polymers, synthetic or semi-synthetic polymers including acrylates, carboxylates, sulfated polymers, nonionic agents such as polaxomers, polyols, and silicone based compounds or a mixture thereof.

Coloring agents can also be included. Examples of these include natural carmine, chlorophyls, curcumin and annatto as well as paint-based colors, caramel colors, and FD&C synthetic coloring agents. Binding and anti-cracking agents which can be employed include materials such as natural gums, starch and cellulose as well as other polysaccharides and polysaccharide derivatives, fatty alcohols fatty esters, paraffin, lanolin and lanolin derivatives, hydrogenated oils, glycerides, and ammonium and alkali metal salts.

Suitable perfuming agents can be of natural or synthetic origin. Examples of brightening and UV-absorbing agents include materials such as tinopal while brightening agents can include materials such as titanium dioxide. Materials such as glycerine can be used as transparency imparting agents.

Examples of thixotropic agents which can be employed in the present invention include natural and modified gums and polysaccharides as well as synthetic polymeric compounds as would be know to the skilled artisan.

Solubilizing agents can include water, propylene glycol, ethyl alcohol, fatty alcohols, isopropanol, ethyl acetate, glycolic acid and lactic acid. Foam boosting agents include amine oxides, fatty acid amines, betaines and amphoteric compounds. Examples of emulsifying agents include lecithin, polysorbate 60, polysorbate 65, polysorbate 80, sucrose fatty acid esters, and salts of stearoyl 2-lactylate.

Abrasive agents include materials such as silica, plant seed-coat powders and clays. Skin healing and rejuvenating agents include various plant oils, plant extracts, sea weeds, and sea dwelling organisms. Suitable antioxidants include natural and synthetic antioxidants including ascorbic acid vitamin E and flavanoids.

The embodiment of the invention is illustrated by following examples, which are to be considered to be illustrative and not limitative for the concept of invention. Examples 1 and 2 show enhancement of microbicidal properties of the anionic surfactant ingredients when used in the composition of syndet bar soap.

EXAMPLE 1

A syndet bar soap was prepared to include the following components:

| Ingredient | w/w % |
| --- | --- |
| Sodium oocoyl isethionate* (83%) | 1.85 |
| Citric acid | 16.27 |
| Sodium sulfate | 81.88 |

*present as Igepon AC-78.

One percent of the preparation was dissolved in neutral water. The pH of the resulting solution was tested and was found to be below 5.0. Microbicidal properties of the solution was evaluated against gram positive *Staphylococcus aureus* and gram negative *Escherichia coli* by using the Association of Analytical Chemist (AOAC) germicidal and detergent sanitizer test. The composition in Example 1 was tested for bactericidal properties essentially by the modified the AOAC (Association of Analytical Chemists) germicidal and detergent sanitizer test using *Staphylococcus aureus* ATCC 6538 and *Escherichia coli* ATCC 11229 using the procedure of Method No. 6 from the 13$^{th}$ Edition of the *Official Methods of Analysis of the A.O.A.C.*, 1111 North 19$^{th}$ Street, Alexandria, Va. 22209. The results are presented in Table I.

As can be seen form the data collected in Table I, under acidic conditions below pH of 5.0, ingredients suitable for syndet bar soap preparation exhibit rapid antimicrobial activities useful for cleaning and disinfecting surfaces.

TABLE I

Percent lethal action of Sodium isethionate after contact time (in seconds)

|  | 30 sec | 60 sec |
| --- | --- | --- |
| *Staphylococcus aureus* | >99,999 | >09,999 |
| *Escherichia coli* | >99,999 | >99,999 |

EXAMPLE II

A syndet bar soap was prepared to include the following components:

| Ingredient | w/w % |
| --- | --- |
| Sodium lauryl sulfosuccinate** (65%) | 2.35 |
| Citric acid | 16.19 |
| Sodium sulfate | 81.46 |

**present as Lathanol LAL.

One percent weight of the above preparation was dissolved in neutral water. The pH of the solution was tested and was found to be below 5.0. The microbicidal properties of the solutions were evaluated against gram-positive *Staphylococcus aureus* and gram negative *Escherichia coli* by using the Association of Analytical Chemist germicidal and detergent sanitizer test. (AOAC) germicidal and detergent sanitizer test. The composition in Example II was tested for bactericidal properties essentially by the modified the AOAC (Association of Analytical Chemists) germicidal and detergent sanitizer test using *Staphylococcus aureus* ATCC 6538 and *Escherichia coli* ATCC 11229 using the procedure of Method No. 6 from the 13$^{th}$ Edition of the *Official Methods of Analysis of the A.O.A.C.*, 1111 North 19$^{th}$ Street, Alexandria, Va. 22209. The results are presented in Table II. As can be seen form the data collected in Table II, under acidic conditions below pH of 5.0, ingredients suitable for syndet bar soap preparation exhibit rapid antimicrobial activities useful for cleaning and disinfecting surfaces.

TABLE II

Percent lethal action of Sodium sulfoacetate after contact time (in seconds)

|  | 30 sec | 60 sec |
| --- | --- | --- |
| *Staphylococcus aureus* | >99.999 | >99.999 |
| *Escherichia coli* | <99.999 | <99.999 |

EXAMPLE III

Composition of Acidic Syndet Bar Soap

| Ingredient | % w/w |
| --- | --- |
| Sodium isethionate | 85.0 |
| Citric acid | 4.0 |
| Stearic acid | 5.0 |
| Titanium dioxide | 0.5 |
| Decyl lactylate | 3.0 |
| Sodium chloride | 0.5 |
| Soluble starch | 2.0 |

Sodium isethionate (Jordepon Cl 60) was first heated to melt between 60–65 degrees C. and then mixed with all other ingredients at 50 degrees C. The mixture was poured into mold arid allowed to harden to make a syndet soap bar.

EXAMPLE IV

Composition of Acidic Syndet Bar Soap

| Ingredient | % w/w |
| --- | --- |
| Sodium isethionate | 81.43 |
| Lactic acid (88%) | 9.46 |
| Titanium dioxide | 0.47 |
| Decyl lactylate | 2.84 |
| Sodium chloride | 0.47 |
| Soluble starch | 1.51 |
| Sucrose coacoate | 3.78 |
| Gardenia perfume | 0.04 |

Syndet soap bar was prepared as explained in example 3. To check the pH of the formulated syndet bar, 1 g of the product was emulsified with deionized neutral water to measure the pH. The pH value of both these products was below 5.0.

What is claimed is:

1. A bar soap preparation having enhanced antibacterial and microbial properties, the bar soap consisting of:
   (A) from about 0.1 weight % to about 95 weight % of at least one anionic surfactant based on the total weight of the preparation;
   (B) at least one acidifying agent present in an amount sufficient to impart a pH of below 5.0, in aqueous solution the acidifying agent being at least one acidifying agent selected from the group consisting of acetic acid, adipic acid, benzoic acid, citric acid, dehydroacetic acid, erythorbic acid, fumaric acid, glutaric acid, gluconic acid, hyaluronic acid, hydroxyacetic acid, lactic acid, malic acid, sorbic acid, succinic acid, tannic acid, tartaric acid, sulfuric acid, phosphoric acid, nitric acid, hydrochloric acid, sulfamic acid, poly lactic acid or poly lactic-glycolic acid, wherein microbial protection results from reduction of the microbial population;
   (C) at least one antibacterial agent selected from the group consisting of benzoic acid salts, esters of benzoic acid, sorbic acid salts, esters of sorbic acid, alkyl esters of para hydroxy benzoic acid, chlorohexidine, imidazolidinyl urea, isothiazolin compounds, triclosan, dehydroacetate, o-phenyl phenol, quaternium compounds, boric acid, formaldehyde solution, butylated hydroxyanisole, butylated hydroxy toluene, fatty acids, fatty acid salts and antibacterial peptides;

(D) at least one lubricating agent selected from the group consisting of xanthan, arabic, ghatti, carrageenan gums, starch, cellulose, alginic acid, dextrans, starch and cellulose polymers, acrylates, carboxylates, sulfated polymers, polaxomers, and silicone based compounds, wherein the at least one skin conditioning agent is present in an amount present between 0.001% by weight and 5.0% by weight;

(E) at least one skin conditioning agent selected from the group consisting of aloe Vera, sea weed extracts, hydrolyzed proteins products, lanolin, lanolin esters, vitamins A, vitamin C, vitamin D, and wherein the at least one skin conditioning agent is present in an amount present between 0.001% by weight and 5.0% by weight;

(F) at least one coloring agent selected from the group consisting of which includes natural carmine, chlorophyl, curcumin, annatto, plant based colors, caramel color, and FD&C coloring agents, wherein the coloring agent is present in an amount less than 5.0% by weight;

(G) at least one moisturizing agent selected from the group consisting of hyaluromc acid, maize amino acids, soluble collagen, glycerine, sorbitol, silk amino acids, polyethylene glycol, panthenol and gluconate, wherein the moisturizing agent is present in an amount less than 5.0% by weight;

(H) at least one binding and anti-cracking agent selected from the group consisting of natural gums, polysaccharides, fatty alcohol, paraffin, lanolin, hydrogenated oils, glycerides, wherein the binding and anti-cracking agent is present in an amount less than 5.0% by weight;

(I) at least one thixotropic agent selected from the group consisting of modified gums, and synthetic polymer compounds, wherein the thixotropic agent is present in an amount less than 5.0% by weight;

(J) at least one solubilizing agent selected from the group consisting of water, propylene glycol, ethyl alcohol, fatty alcohols, isopropanol, ethyl acetate, wherein the solubilizing agent is present in an amount less than 5.0% by weight;

(K) at least one emulsifying agent selected from the group consisting of lecithin, polysorbate 60, polysorbate 65, polysorbate 80, sucrose fatty acid esters and salts of stearyl 2-lactylate, wherein the emulsifying agent is present in an amount less than 5.0% by weight;

(L) at least one abrasive agent selected from the group consisting of silica, plant seed coat powders and clays, wherein the abrasive agent is present in an amount less than 5.0% by weight and;

(M) at least one antioxidant agent selected from the group consisting of ascorbic acid, vitamin E and flavanoids, wherein the antioxidant agent is present in an amount less than 5.0% by weight.

2. The bar soap of claim 1 wherein the anionic surfactant is present as either a free acid, an ester or as a salt form of at least one anionic surfactant compound.

3. The bar soap of claim 1 wherein the anionic surfactant is present as either a free acid, an ester or as a salt form of at least two different anionic surfactant compounds.

4. The bar soap composition of claim 3 wherein the anionic surfactant is at least one of the following compounds:

(A) $C_6$–$C_{18}$ alkyl- and alkenyl sulfates;

(B) $C_8$–$C_{18}$ alkyl- and alkenyl-ether sulfates;

(C) $C_8$–$C_{16}$ alkyl diphenyl ether disulfonates;

(D) $C_4$–$C_{18}$ fatty acid isethionates;

(E) $C_6$–$C_{18}$ alkyl- and alkenyl sulfonates;

(F) dialkyl- and dialkenyl sulfosuccinates in which the alkyl or alkenyl groups independently contain from six to eighteen carbon atoms;

(G) $C_6$–$C_{18}$ alkyl benzene sulfonates;

(H) alkyl naphthalene sulfonates in which alkyl group contains from one to six carbon atoms;

(I) mono-n-alkyl and mono-n-alkenyl acyl esters of $C_2$–$C_4$ hydroxylated monocarboxylic acids in which the alkyl or alkenyl group contains from six to eighteen carbon atoms;

(J) mono-n-alkyl and mono-n-alkenyl acyl esters of $C_2$–$C_4$ hydroxylated dicarboxylic acids in which the alkyl or alkenyl group contains six to eighteen carbon atoms;

(K) mono-n-alkyl and mono-n-alkenyl alkyl esters of $C_2$–$C_4$ dicarboxylic acids in which the alkyl or alkenyl group contains from six to eighteen carbon atoms; and (L) $C_4$–$C_{18}$ fatty alcohol sulfoacetates, and mixtures of two or more said surfactants.

5. The bar soap preparation of claim 1 wherein the at least one antimicrobial agent is present in an amount between 0.001% by weight and 5.0% by weight.

6. A bar soap preparation having enhanced antibacterial and microbial properties, the bar soap consisting of:

(A) from about 0.1 weight % to about 95 weight % based on the total weight of at least one anionic surfactant, selected from the group consisting of alkali metal salts of alpha olefin sulfonate, alkali metal salts of cocoyl isethionate, alkali metal salts of lauryl sulfoacetate and alkali metal salts of decyl lactylate;

(B) at least one acidifying agent present in an amount sufficient to impart a pH of below 5.0, the at least one acidifying agent taken from the group which includes lactic acid, citric acid, ascorbic acid, erythorbic acid, malic acid, and adipic acid, wherein microbial protection results from reduction of the microbial population on the contact surface;

(C) at least one antibacterial agent selected from the group consisting of benzoic acid salts, esters of benzoic acid, sorbic acid salts, esters of sorbic acid, alkyl esters of para hydroxy benzoic acid, chlorohexidine, imidazolidinyl urea, isothiazolin compounds, triclosan, dehydroacetate, o-phenyl phenol, quaternium compounds, boric acid, formaldehyde solution, butylated hydroxyanisole, butylated hydroxy toluene, fatty acids, fatty acid salts and antibacterial peptides;

(D) at least one lubricating agent selected from the group consisting of xanthan, arabic, ghatti, carrageenan gums, starch, cellulose, alginic acid, dextrans, starch and cellulose polymers, acrylates, carboxylates, sulfated polymers, polaxomers, and silicone based compounds, wherein the at least one skin conditioning agent is present in an amount present between 0.001% by weight and 5.0% by weight;

(E) at least one skin conditioning agent selected from the group consisting of aloe Vera, sea weed extracts, hydrolyzed proteins products, lanolin, lanolin esters, vitamins A, vitamin C, vitamin D, and wherein the at least one skin conditioning agent is present in an amount present between 0.001% by weight and 5.0% by weight;

(F) at least one coloring agent selected from the group consisting of which includes natural carmine, chlorophyl, curcumin, annatto, plant based colors, caramel color, and FD&C coloring agents, wherein the coloring agent is present in an amount less than 5.0% by weight;

(G) at least one moisturizing agent selected from the group consisting of hyaluromc acid, maize amino acids, soluble collagen, glycerine, sorbitol, silk amino acids, polyethylene glycol, panthenol and gluconate, wherein the moisturizing agent is present in an amount less than 5.0% by weight;

(H) at least one binding and anti-cracking agent selected from the group consisting of natural gums, polysaccharides, fatty alcohol, paraffin, lanolin, hydrogenated oils, glycerides, wherein the binding and anti-cracking agent is present in an amount less than 5.0% by weight;

(I) at least one thixotropic agent selected from the group consisting of modified gums, and synthetic polymer compounds, wherein the thixotropic agent is present in an amount less than 5.0% by weight;

(J) at least one solubilizing agent selected from the group consisting of water, propylene glycol, ethyl alcohol, fatty alcohols, isopropanol, ethyl acetate, wherein the solubilizing agent is present in an amount less than 5.0% by weight;

(K) at least one emulsifying agent selected from the group consisting of lecithin, polysorbate 60, polysorbate 65, polysorbate 80, sucrose fatty acid esters and salts of stearyl 2-lactylate, wherein the emulsifying agent is present in an amount less than 5.0% by weight;

(L) at least one abrasive agent selected from the group consisting of silica, plant seed coat powders and clays, wherein the abrasive agent is present in an amount less than 5.0% by weight and;

(M) at least one antioxidant agent selected from the group consisting of ascorbic acid, vitamin E and flavanoids, wherein the antioxidant agent is present in an amount less than 5.0% by weight.

\* \* \* \* \*